United States Patent [19]

Nakazawa

[11] Patent Number: 5,759,513

[45] Date of Patent: Jun. 2, 1998

[54] APPARATUS AND PROCESS FOR PREPARING RADIOISOTOPE-LABELED REAGENT

[76] Inventor: Nobuhiko Nakazawa, 21-2, Karabe 4-chome, Narita-shi, Chiba, Japan

[21] Appl. No.: 607,883

[22] Filed: Feb. 27, 1996

[51] Int. Cl.[6] .......................... A61K 51/00; A61M 36/14
[52] U.S. Cl. ................. 424/1.11; 424/1.81; 424/1.89; 422/903
[58] Field of Search ........................... 424/1.11, 1.61, 424/1.65, 1.81, 1.37, 1.85, 1.89; 206/223, 569, 570; 534/10–16; 422/50, 61, 903

[56] References Cited

U.S. PATENT DOCUMENTS 3,986,835  10/1976  Takagi ............................. 23/259
5,645,801  7/1997  Bouma et al. .................. 422/68.1

OTHER PUBLICATIONS

Masterton et al (1985), Chemical Principles, Sixth Edition, pp. 23–28, "Separation of mixtures".

*Primary Examiner*—John Kight
*Assistant Examiner*—Dameron Jones
*Attorney, Agent, or Firm*—Oblon, Spivak, McClelland, Maier & Neustadt, P.C.

[57] ABSTRACT

Apparatus and process for non-pyrogenously preparing a radioisotope-labeled reagent that includes a plurality of raw material-holding containers, reaction vessels, and columns connected to each other by transfer tubes that are hermetically sealed such that the raw materials can be introduced into the appropriate reaction vessels in the appropriate order through the transfer tubes using a force fed inert gas.

6 Claims, 3 Drawing Sheets

1

APPARATUS AND PROCESS FOR PREPARING RADIOISOTOPE-LABELED REAGENT

BACKGROUND OF THE INVENTION

1. Field of the Invention

The present invention relates to an improved process for preparing a radioisotope-labeled reagent, and more particularly to a process for preparing a reagent labeled with a radioisotope having a short half-life, which is suitable for use in research on morbidity, diagnoses of diseases and the like.

2. Description of the Background Art

Radioisotope-labeled reagents are widely used in a medical field and tend to increase in importance, particularly, to research on morbidity and diagnoses of diseases. Since the radioisotope-labeled reagents are often administered to the human and animal, they are required to have, in particular, sterility and nonpyrogenicity, as well as uniform quality (there is no difference in quality between lots or between plants) when used particularly for diagnose.

Of these radioisotope-labeled reagents, diagnostic reagents having a very short half-life have heretofore been prepared by means of their special automatic synthesizers. In this means, however, raw materials and reagents necessary for synthesis have to be exactly weighed and filled at every synthesis under the necessity of preparing them right before their use due to the short half-life of an isotope used. In addition, it takes a long time for the weighing and filling operation thereof in view of the sterility, nonpyrogenicity and uniform quality, and such management has been difficult. In particular, a proportion of the preparatory time required of these raw materials for synthesis to the time required of one diagnosis or inspection making use of a reagent labeled with a radioisotope having a very short half-life is high, and there has thus been a demand for shortening of such preparatory time.

SUMMARY OF THE INVENTION

It is accordingly an object of the present invention to shorten the preparatory time required of synthesis or preparation in the preparation of a radioisotope-labeled reagent and make the management of sterility, nonpyrogenicity and a difference in quality between lots or between plants more easy.

The present inventor has carried out various investigations with a view toward solving the above problems. As a result, it has been found that when a prefilled kit in a closed system in which necessary amounts of all raw materials other than a raw material for a radioisotope having a short half-life have been filled in advance is set in an automatic synthesizer to use it, a reagent labeled with the radioisotope can be easily synthesized in a short period of time without a difference in quality between lots or between plants while retaining sterility and nonpyrogenicity, thus leading to completion of the present invention.

According to the present invention, there is thus provided a prefilled kit for preparing a radioisotope-labeled reagent, comprising a plurality of raw material-holding containers, a plurality of reaction vessels, the required number of columns, transfer tubes suited to reaction processes through which the containers, reaction vessels and columns are connected to one another, and shut-off cocks provided in the individual connections, wherein necessary amounts of all raw materials other than a raw material for a radioisotope, which the amounts are calculated according to a necessary amount of the intended radioisotope-labeled compound, are hermetically held in advance in the suitable reaction vessels or the suitable holding containers from which the raw materials are introduced into their corresponding reaction vessels, which the vessels and containers are placed in a reaction system apparatus to which sources of force-feed gas and pressure reduction can be connected through respective shut-off cocks in order that liquids may be transferred to the intended containers and reaction vessels by means of a nonreactive gas for force feed and pressure reduction.

In the prefilled kit, the kit may be combined with a system in which the opening and closing of the shut-off cocks for connection, the shut-off cocks for force-feed gas and the pressure reducing cocks are controlled in advance by a computer program in accordance with the time series of the order of opening and closing, and the start and stop of liquid-transfer pumps, which the time series is suited to the preparation process of the intended radioisotope-labeled reagent.

According to the present invention, there is also provided a process for preparing a radioisotope-labeled reagent, which comprises using a prefilled kit for preparing a radioisotope-labeled reagent, which includes a plurality of raw material-holding containers, a plurality of reaction vessels, the required number of columns, transfer tubes suited to reaction processes through which the containers, reaction vessels and columns are connected to one another, and shut-off cocks provided in the individual connections, wherein necessary amounts of all raw materials other than a raw material for a radioisotope, which the amounts are calculated according to a necessary amount of the intended radioisotope-labeled compound, are hermetically held in advance in the suitable reaction vessels or the suitable holding containers from which the raw materials are introduced into their corresponding reaction vessels, which the vessels and containers are placed in a reaction system apparatus to which sources of force-feed gas and pressure reduction can be connected through respective shut-off cocks in order that liquids may be transferred to the intended containers and reaction vessels by means of a nonreactive gas for force feed and pressure reduction; and introducing a raw material for a radioisotope into the kit to conduct a reaction.

In the preparation process, the prefilled kit may be combined with a system in which the opening and closing of the shut-off cocks for connection, the shut-off cocks for force-feed gas and the pressure reducing cocks are controlled in advance by a computer program in accordance with the time series of the order of opening and closing, and the start and stop of liquid-transfer pumps, which the time series is suited to the preparation process of the intended radioisotope-labeled reagent.

The above and other objects, features and advantages of the present invention will become apparent from the following description of preferred embodiments with reference to the accompanying drawings.

BRIEF DESCRIPTION OF THE DRAWINGS

In FIG. 1, reference numerals 1, 2, 3, 4, 5, 6, 7, 8, 9, 10, 11, 12, 13, 14, 15, 16, 17, 18, 19, 20, 21, 22, 23, 24, 25, 26, 27, 28 and 29 designate shut-off cocks, while reference numerals 30, 31, 32, 33, 34 and 35 indicate bacterial filters. Reference characters D, F, M, S, T and R designate reaction vessels, reference characters B, C, G, H, I, Q, V and K indicate raw material-holding containers, and reference characters A, L, N, P and O designate columns.

In FIG. 2, reference numerals 1, 2, 3, 4, 5, 6, 7, 8, 9, 10, 11, 12, 13, 14, 15, 16, 18, 19, 20 and 21 designate shut-off cocks, while reference numerals 22, 23, 24, 25 and 26 indicate bacterial filters. Reference characters A, B, C, G, P, N, Q and H indicate raw material-holding containers, reference characters K, L and M designate reaction vessels, reference characters J, D and E designate columns, and reference character I indicates a stainless steel trap.

In FIG. 3, reference numerals 1, 2, 3, 4, 5, 6, 7, 8, 9, 10, 11, 12 and 13 designate shut-off cocks, while reference numerals 14, 15, 16, 17 and 18 indicate bacterial filters. Reference characters K and I designate reaction vessels, reference characters C, D and E indicate raw material-holding containers, reference characters A, G and H designate columns, and reference character B indicates a stainless steel trap.

DETAILED DESCRIPTION OF THE PREFERRED EMBODIMENTS

Figure 1:
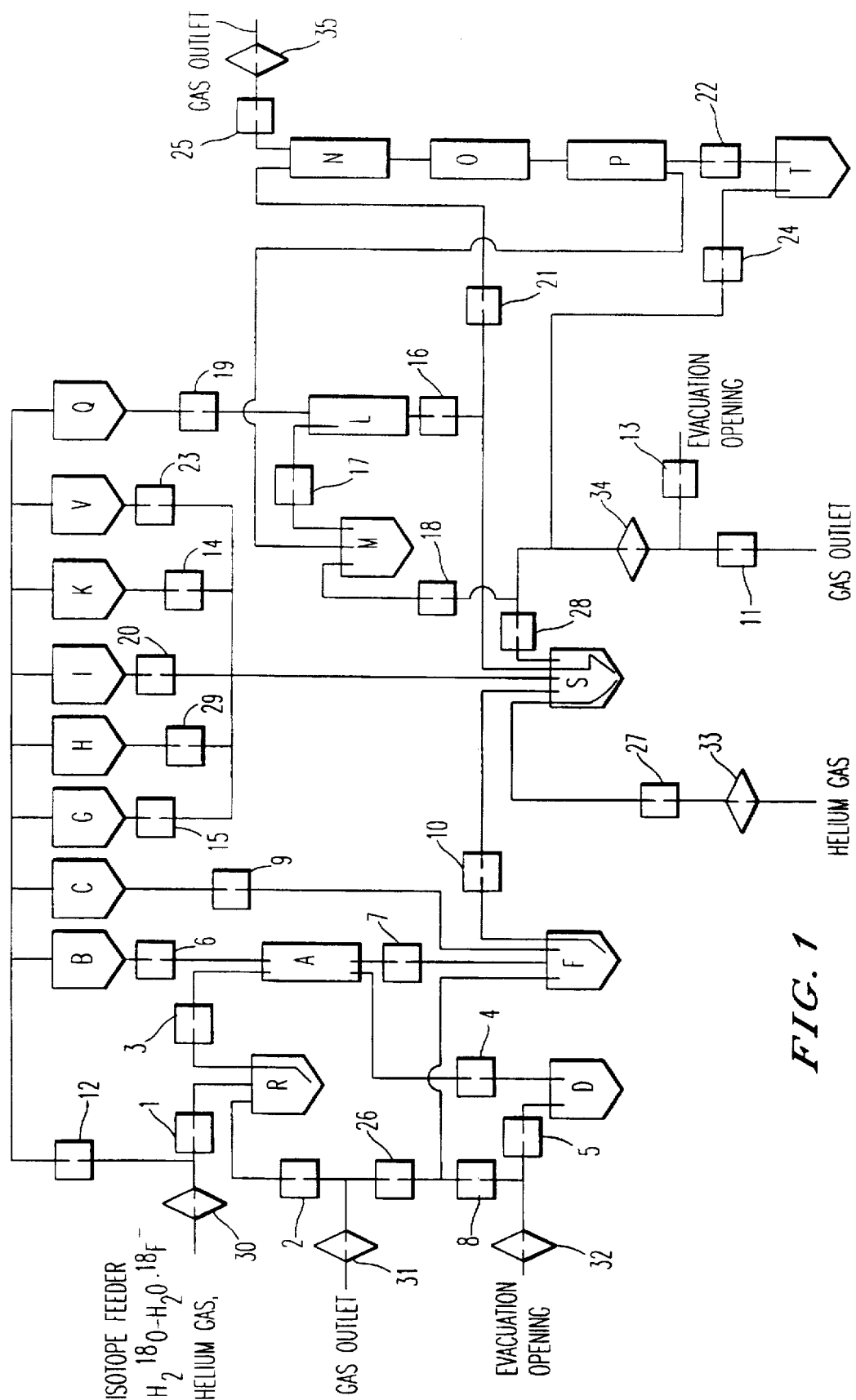
FIG. 1 illustrates an example of a prefilled kit for preparing $^{18}$F-FDG.

Prefilled kits for preparing a radioisotope-labeled reagent according to the present invention include raw material-holding containers, reaction vessels and columns which are connected to one another through transfer tubes. In these kits, the feed of raw materials to the reaction vessels, their reaction, and separation and purification can be performed in a closed system. These kits feature that all raw material other than a raw material for a radioisotope are filled therein. Such raw materials are filled in necessary amounts according to the amount of the intended labeled compound.

The raw materials are desirably liquid. They may be filled in the form of a solid in some cases. In such a case, they are dissolved in a solvent used in a reaction, as needed, to be transferred to the respective reaction vessels for use.

The individual raw materials and intermediate products are transferred by means of a nonreactive gas for force feed and pressure reduction. Such transfer is controlled by opening and/or closing shut-off cocks provided in the individual connections. The transfer and reactions (heating, cooling, stirring, etc.) are desirably computer-controlled.

When a reaction is performed by means of the kit according to the present invention, it is only necessary to introduce a radioisotope such as $^{11}$C, $^{15}$O, $^{13}$N or $^{18}$F into the kit to react it. Preferable examples of the radioisotope include $^{11}$C-carbon dioxide, $^{15}$O$_2$, $^{13}$NOx and $^{18}$F$^-$, which are produced by a cyclotron.

Preferable examples of the intended products synthesized by the kits according to the present invention include $^{18}$F-fluorodeoxyglucose ($^{18}$F—FDG), $^{11}$C-methionine, $^{15}$O—CO$_2$, $^{13}$N—NH$_3$ and $^{11}$C-acetic acid.

As a actual operation of a reaction, the prefilled kit is set in an apparatus by which the heating or cooling of the reaction vessels, and opening and/or closing of the shut-off cocks provided between the raw material-holding containers and the reaction vessels, and the like are computer-controlled, and a radioisotope inlet, gas outlet(s), evacuation opening(s) and gas inlet(s) of the prefilled kit are connected to a radioisotope feeder, exhaust system(s), evacuation system(s) and gas feeder(s), respectively.

The shut-off cocks are then opened in order from the side of the radioisotope inlet to allow a chemical preparation process of the intended labeled reagent to proceed, thereby finally obtaining a labeled reagent which can be administered to the human body.

According to the present invention, raw materials and the like can be prefilled into containers in a sterile room. Therefore, various bacteria and pyrogens are hardly mixed in. Besides, a bacterial filter is attached to an opening of each of the filled containers, after which the container can be sterilized, so that the filled containers are completely sterilized and made nonpyrogenic. Accordingly, their sterility and nonpyrogenicity can be ensured when conducting sampling inspection from a lot.

Since the individual raw materials can be subdivided by the same technique, and prefilled kits can be formulated as the same lot, the quality of a labeled reagent, the difference of which may arise between plants at every labeled reagent, is prevented from being affected by the quality of the raw materials and differences in weighing and subdividing techniques.

When a labeled reagent is newly prepared after a radioisotope-labeled reagent prepared with this kit is used and decayed to some extent, the raw materials are easily set in an automatic synthesizer, so that the preparation is completed in a short period of time, and an operator gets off with a small radiation exposure.

The present invention will hereinafter be described in detail by the following examples. However, it should be borne in mind that this invention is not limited to and by these examples.

EXAMPLE 1

Prefilled Kit for Preparing $^{18}$F-Fluorodeoxyglucose ($^{18}$F—FDG)

A prefilled kit for preparing the title reagent according to this example was devised with reference to the method described in K. Hamacher, et al., Applied Radiation and Isotope, 41, 47 (1990). The construction thereof is illustrated in FIG. 1.

The synthetic process of this labeled reagent may be expressed by the following reaction scheme:

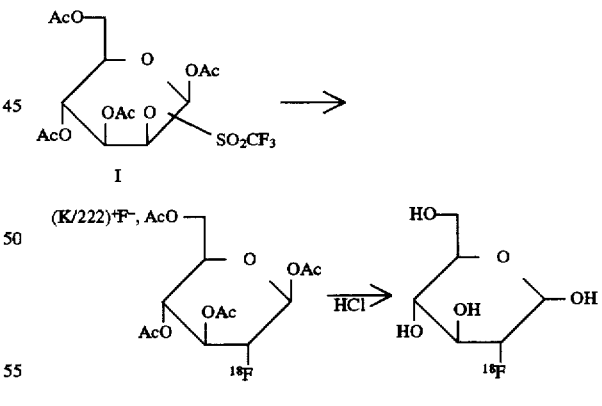

wherein I is 1,3,4,6-tetra-O-acetyl-2-O-trifluoromethanesulfonyl-β-D-mannopyranose, II is $^{18}$F-fluorodeoxyglucose ($^{18}$F—FDG), and K/222 is an aminopolyether potassium complex.

Cocks 1 and 2 illustrated in FIG. 1 are first opened to cause H$_2$$^{18}$O—H$_2$O.$^{18}$F$^-$ to flow out of a radioisotope feeder by helium gas, thereby transferring it to a reaction vessel R.

The cock 2 is closed, and cocks 3, 4 and 5 are opened to transfer H$_2$$^{18}$O—H$_2$O.$^8$F$^-$ present in the reaction vessel R to a column A (anion exchange resin, AG1×8, 10 mg) while pressurizing by helium gas, thereby adsorbing $^{18}F^-$ on the column A and recovering $H_2{}^{18}O$—$H_2O$ in a reaction vessel D.

The cocks 3, 4 and 5 are closed, and cocks 9, 12 and 26 are opened to transfer a solution of 320 mg of Kryptofix 222 (K/222) in 1.5 ml of acetonitrile, which is contained in a container C, to a reaction vessel F.

The cocks 9 and 26 are closed, and cocks 6, 7 and 8 are opened to cause a solution of 30 mg of $K_2CO_3$ in 0.3 ml of water, which is contained in a container B, to flow into the column A, thereby eluting $^{18}F^-$ and transferring to the reaction vessel F. The cocks 6, 7 and 8 are closed, and cocks 9, 10, 11 and 28 are opened to transfer a solution containing $^{18}F^-$.Kryptofix 222, $K_2CO_3$, water and acetonitrile, which is contained in the reaction vessel F, to a reaction vessel S by helium gas. The cocks 9 and 10 are closed, a cock 27 is opened, and the temperature of the reaction vessel S is raised to 50° C. while bubbling with helium gas. A cock 13 is opened and the cock 11 is closed to maintain the pressure inside the reaction vessel S to 600 millibar, and in the meantime, the solvent is evaporated to dryness.

The temperature of the reaction vessel S is raised to 105° C., and the cock 27 is closed to continue the evaporation to dryness further for 5 minutes.

A cock 14 is opened to transfer a solution of 20 mg of 1,3,4,6-tetra-O-acetyl-2-O-trifluoromethane-sulfonyl-β-D-mannopyranose in 1 ml of acetonitrile, which is contained in a container K, to the reaction vessel S. The cock 14 is closed, the cock 27 is opened, and the temperature of the reaction vessel S is raised to 85° C. while bubbling with helium gas, thereby distilling off acetonitrile under reduced pressure.

A cock 15 is opened to transfer 5 ml of 5 mM HCl contained in a container G to the reaction vessel S. The cock 15 is closed, and 10 seconds later, cocks 16, 17 and 18 are opened, and the cock 28 is closed, whereby the solution in the reaction vessel S is caused to pass through a column L (Seppack C18) and collected in a reaction vessel M.

The cocks 16, 17 and 18 are closed, and the cock 28 and a cock 29 are opened to transfer 5 ml of 5 mM HCL contained in a container H to the reaction vessel S. The cock 29 is closed, and 10 seconds later, the cocks 16, 17 and 18 are opened, and the cock 28 is closed, whereby the extract in the reaction vessel S is caused to pass through the column L and collected in the reaction vessel M. The cocks 18 and 27 are closed, and a cock 19 and the cock 28 are opened, whereby 3 ml of tetrahydrofuran contained in a container Q are caused to pass through the column L to elute $^{18}F$—FDG adsorbed on the column L to transfer to the reaction vessel S.

The cocks 16 and 19 are closed, the cock 27 is opened, and the temperature of the reaction vessel S is maintained at 50° C. while bubbling with helium gas, thereby distilling off tetrahydrofuran.

The cock 27 is closed, and a cock 20 is opened to transfer 2 ml of 2 M HCl contained in a container I to the reaction vessel S. The cocks 13 and 20 are closed, and the temperature of the reaction vessel S is raised to 120° C. to heat it for 15 minutes. During the heating, the pressure inside the reaction vessel S is maintained at 1.9–2.0 bar by operating the cock 11.

After the reaction vessel S is cooled to room temperature, the cocks 28 and 11 are closed, and the cocks 13 and 27 and cocks 21, 22 and 24 are opened, whereby the reaction mixture contained in the reaction vessel S is caused to pass through columns N (AGII-A8), O (Seppack C-18) and P (Seppack Alumina) and to flow into a reaction vessel T containing 1.2 ml of 10% saline.

After the cocks 24 and 27 are closed, a cock 23 and the cock 28 are opened to transfer 10 ml of water contained in a container V to the reaction vessel S. The cocks 23 and 28 are then closed, and the cocks 24 and 27 are opened, whereby washings in the reaction vessel S are caused to pass through the columns N, O and P and transferred to the reaction vessel T.

In this case, a radiation detector or the like is used, and the cocks 18, 22 and 25 are also utilized so as to transfer only a liquid high in radioactivity to the reaction vessel T, thereby obtaining a solution of $^{18}F$—FDG.

EXAMPLE 2

Prefilled Kit for Preparing $^{11}C$-Methionine

A prefilled kit for preparing the title reagent according to this example was devised with reference to the method described in C. Marazano, et al., International Journal of Applied Radiation and Isotopes, 28, 49 (1977), and the like. The construction thereof is illustrated in FIG. 2.

The synthetic process of this labeled reagent may be expressed by the following reaction scheme:

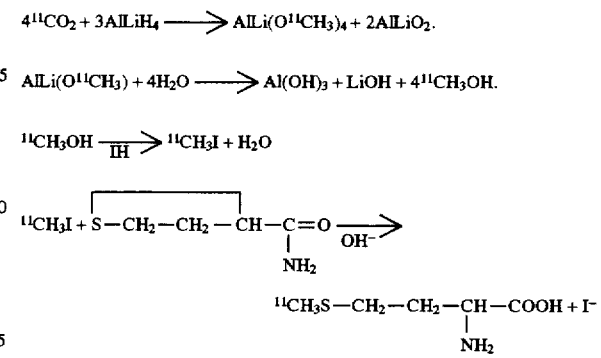

Figure 2:
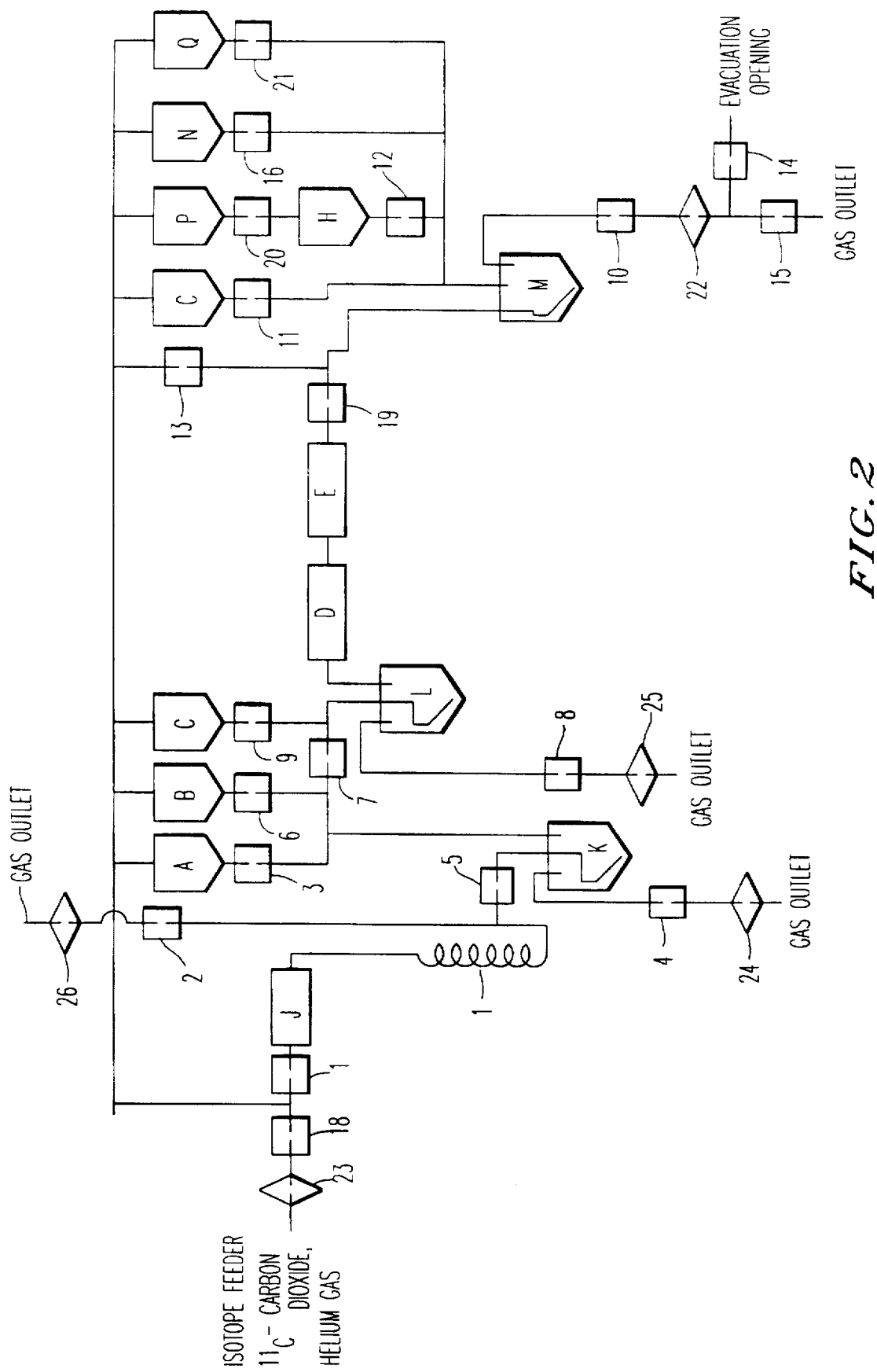
FIG. 2 illustrates an example of a prefilled kit for preparing $^{11}$C-methionine.

After a stainless steel trap I of 0.2 mm across by 40 cm long as illustrated in FIG. 2 is refrigerated with liquid nitrogen, cocks 18, 1 and 2 are opened, whereby $^{11}C$-carbon dioxide is forced out of a radioisotope feeder by helium gas, caused to pass through a column J packed with 0.7 g of $P_2O_5$ and trapped in the trap I.

The cocks 1 and 2 are closed, and cocks 3 and 4 are opened, thereby transferring a solution of 95 μg of lithium aluminum hydride in 100 μl of tetrahydrofuran, which is contained in a container A, to a reaction vessel K.

The cock 3 is closed, the reaction vessel K is refrigerated to −15° C., a cock 5 is opened, and the cock 1 is opened while heating the trap I back to room temperature, whereby $^{11}C$-carbon dioxide is transferred to the reaction vessel K containing the tetrahydrofuran solution of lithium aluminum hydride by helium gas.

The reaction vessel K is maintained at 60° C. to distill off tetrahydrofuran while bubbling with helium gas.

Cocks 8 and 9 are opened to transfer 200 μl of 67% hydroiodic acid contained in a container C to a reaction vessel L. The cocks 1, 8 and 9 are closed, and a cock 6 is opened to transfer 100 μl of water contained in a container B to the reaction vessel K. The cock 6 is closed, and cocks 10, 11 and 15 are open to transfer 200 μl of ethyl alcohol contained in a container G to a reaction vessel M.

The cock 11 is closed, cocks 19 and 7 are opened, the cock 4 is closed, and the cock 1 is open while raising the temperatures of the reaction vessels K and L to 160° C. and 180° C., respectively, thereby transferring $^{11}C$-methanol formed in the reaction vessel K to the reaction vessel L.

$^{11}$C-Methanol transferred to the reaction vessel L is iodinated into $^{11}$C-iodomethanol which is then trapped in ethyl alcohol contained in the reaction vessel M.

After the cock 1 is closed, and the temperature of the reaction vessel M is raised to 60° C., cocks 12 and 20 are opened to transfer 10 mg of L-homocysteine thiolactone hydrochloride contained in a container H to the reaction vessel M by 100 µl of 1M NaOH contained in a container P.

The cocks 12 and 20 are closed, and the reaction vessel M is heated at 70° C. for 7 minutes.

A cock 21 is opened to transfer 100 µl of 1M HCl contained in a container Q to the reaction vessel M. The cocks 15, 21 and 19 are closed, and a cock 13 is opened to cause helium gas to flow into the reaction vessel M, and in the meantime, a cock 14 is opened to distill off a water-ethanol solution contained in the reaction vessel M.

The cocks 13 and 14 are closed, the temperature of the reaction vessel M is lowered, and at the same time, the cock 15 and a cock 16 are opened to transfer 5 ml of physiological saline contained in a container N to the reaction vessel M, thereby obtaining a solution of $^{11}$C-methionine.

EXAMPLE 3

Prefilled Kit for Preparing $^{11}$C-Acetic Acid

Figure 3:
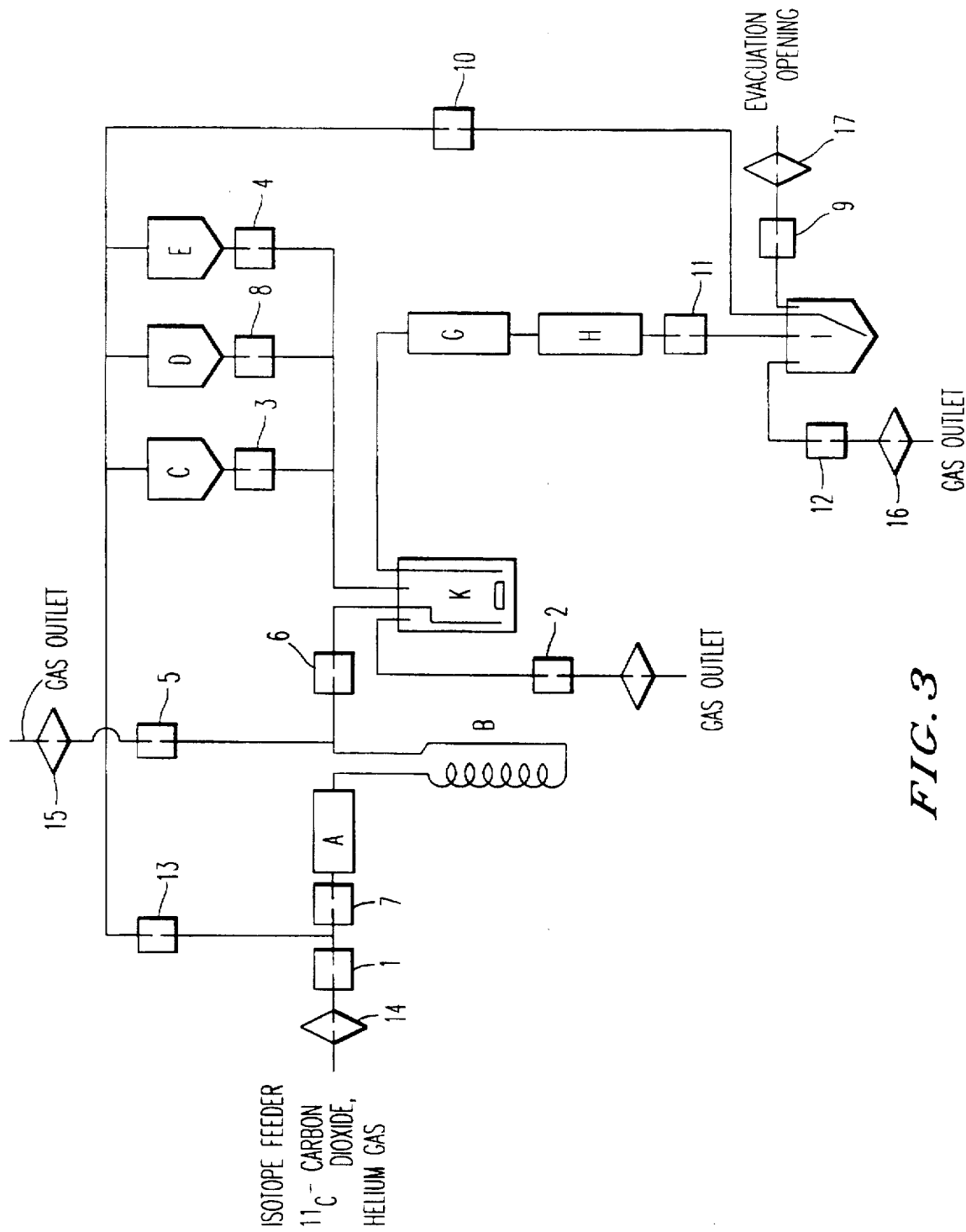
FIG. 3 illustrates an example of a prefilled kit for preparing $^{11}$C-acetic acid.

A prefilled kit for preparing the title reagent according to this example was devised with reference to the method described in V. W. Pike, et al., International Journal of Applied Radiation and Isotopes, 35, 623 (1984). The construction thereof is illustrated in FIG. 3.

The synthetic process of this labeled reagent may be expressed by the following reaction scheme:

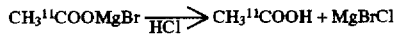

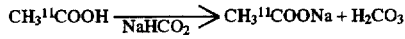

After a stainless steel trap B of 0.2 mm across by 40 cm long as illustrated in FIG. 3 is refrigerated with liquid nitrogen, cocks 1, 5 and 7 are opened, whereby $^{11}$C-carbon dioxide is forced out of a radioisotope feeder by helium gas, caused to pass through a column A packed with 0.2 g of $MgCl_2O_4$ and trapped in the trap B.

The cocks 5 and 7 are closed, and cocks 2, 3 and 13 are opened to transfer 4 ml of a 0.05 mM diethyl ether solution of methylmagnesium bromide contained in a container C to a reaction vessel K.

The cock 3 is closed, a cock 6 is opened, and the trap B is heated back to room temperature. The cock 7 is then opened to transfer $^{11}$C-carbon dioxide to the reaction vessel K containing the diethyl ether solution of methylmagnesium bromide by helium gas.

The cock 6 is closed, and 2 minutes later, a cock 4 is opened to transfer 0.8 ml of 6M HCl contained in a container E to the reaction vessel K while stirring the contents in the reaction vessel K by a stirrer.

After 20 seconds, the cock 4 is closed, and a cock 8 is opened to transfer a mixture of 0.8 ml of 6M NaOH and 10 ml of 0.84% aqueous $NaHCO_3$, which is contained in a container D, to the reaction vessel K. After the contents in the reaction vessel K are stirred for 1 minutes, the stirrer is stopped.

The cock 2 is closed, and cocks 11 and 9 are opened, whereby 10.8 ml of an aqueous solution of $^{11}$C-acetic acid contained in the reaction vessel K are caused to pass through columns G (AgO, 0.2 g) and H (AG50W×8) and transferred to a reaction vessel I.

The cocks 8 and 11 are closed, a cock 10 is opened, and the temperature of the reaction vessel I is raised to 60° C. while bubbling with helium gas, thereby heating the contents in the reaction vessel I for 5 minutes. The temperature thereof is then cooled back to room temperature.

The cocks 9 and 10 are closed, and a cock 12 is opened, thereby obtaining a solution of $^{11}$C-acetic acid.

What is claimed is:

1. An apparatus for preparing a radioisotope-labeled reagent comprising a hermetically sealed unit, comprising:
   a plurality of raw material-holding containers;
   a plurality of reaction vessels;
   a plurality of columns;
   at least one liquid transfer pump;
   a plurality of transfer tubes forming connections among said containers, vessels, columns and pumps;
   shut-off cocks disposed in the containers, vessels, columns, or connections;
   at least one raw material disposed in at least one of said containers, vessels or columns, wherein said material is held within the hermetically sealed unit; and
   a source of force-fed gas connected to at least one of said containers, vessels, columns and tubes, wherein sources of force-fed gas and pressure reduction can be connected through respective shut-off cocks in order that liquids may be transferred to the intended containers and reaction vessels by means of a non-reactive gas for force-fed and pressure reduction, wherein said radioisotope-labeled reagent comprises, as a label, a radioactive atoms of relatively short half-life selected from the group consisting of $^{11}$C, $^{15}$O, $^{13}$N and $^{18}$F.

2. An apparatus according to claim 1, further comprising a system in which the opening and closing of the shut-off cocks for connection, the shut-off cocks for a force-fed gas and the pressure reducing cocks are controlled in advance by a computer program in accordance with the time series of the order of opening and closing, and the start and stop of liquid-transfer pumps, which time series is suited to the preparation process of the intended radioisotope-labeled reagent.

3. An apparatus according to claim 1, wherein the intended radioisotope-labeled reagent is $^{18}$F-fluorodeoxyglucose ($^{18}$F—FDG), $^{11}$C-methionine, $^{15}$O—$CO_2$, $^{13}$N—$NH_3$ or $^{11}$C-acetic acid.

4. A process for preparing a radioisotope-labeled reagent, comprising:
   introducing raw materials into a hermetically sealed unit containing containers, vessels, and columns and hermetically holding the raw materials in the containers, vessels, and columns;
   transferring the raw materials to appropriate reaction vessels and columns by means of force-fed non-reactive gas, pressure reduction and liquid transfer pumps, wherein the appropriate reaction vessels and columns are connected to the containers by transfer tubes; and controlling said transferring of materials by means of shut-off cocks for connection, shut-off cocks for force-fed gas, shut-off cocks for pressure reduction and operation of liquid transfer pumps wherein said radioisotope-labeled reagent comprises, as a label, a radioactive atom of relatively short half-life selected from the group consisting of $^{11}C$, $^{15}O$, $^{13}N$ and $^{18}F$.

5. The process according to claim 4, wherein the opening and closing of the shut-off cocks for connection, the shut-off cocks for force-fed gas and the pressure reducing cocks are controlled in advance by a computer program in accordance with the time series of the order of opening and closing, and the start and stop of liquid-transfer pumps, which time series is suited to the preparation process of the intended radioisotope-labeled reagent.

6. The process according to claim 4, wherein the intended radioisotope-labeled reagent is $^{18}F$-fluoro-deoxyglucose ($^{18}F$—FDG), $^{11}C$-methionine, $^{15}O$—$CO_2$, $^{13}N$—$NH_3$ or $^{11}C$-acetic acid.

* * * * *